United States Patent [19]

Kramer et al.

[11] Patent Number: 5,712,313
[45] Date of Patent: Jan. 27, 1998

[54] PROCESS FOR CARRYING OUT CHEMICAL EQUILIBRIUM REACTIONS

[75] Inventors: Gert Jan Kramer; Jean Paul Lange, both of Amsterdam, Netherlands

[73] Assignee: Shell Oil Company, Houston, Tex.

[21] Appl. No.: 550,135

[22] Filed: Feb. 26, 1996

[51] Int. Cl.$^6$ .......................... B01J 8/04; C07C 29/151; C07C 29/152
[52] U.S. Cl. .................... 518/706; 518/707; 518/724; 518/725; 423/437 M; 423/655; 568/895; 568/896; 568/695; 585/411; 585/412; 585/659
[58] Field of Search .................................. 518/706, 707, 518/724, 725

[56] References Cited

U.S. PATENT DOCUMENTS 4,968,722  11/1990  Westerterp ............................. 518/706

FOREIGN PATENT DOCUMENTS 430699  6/1991  European Pat. Off. .
589342  3/1944  United Kingdom .
2255516  11/1992  United Kingdom .

OTHER PUBLICATIONS

Search Report (Dec. 13, 1995) for GB 9519849.0.

Primary Examiner—Bernard Dentz
Assistant Examiner—Lyman H. Smith
Attorney, Agent, or Firm—Kim Muller

[57] ABSTRACT

A process for carrying out a chemical equilibrium reaction is disclosed in which, in a first stage, one or more reactants are contacted with a fixed arrangement of a catalyst under conditions such that the reactants and the products of the reaction are gaseous, the unconverted reactants and products of the first stage being passed to a second stage, in which they are contacted with a fixed arrangement of a catalyst and the reaction allowed to proceed in the presence of an absorbent capable of absorbing a product of the reaction. There is specifically disclosed a process for the synthesis of methanol from carbon monoxide and hydrogen, in which, in a first stage, carbon monoxide and hydrogen are contacted with a fixed arrangement of a catalyst active in catalyzing the synthesis of methanol under conditions such that the methanol formed is present as a gas under the prevailing reaction conditions, the unconverted carbon monoxide and hydrogen and methanol produced in the first stage being passed to a second stage, in which they are contacted with a fixed arrangement of a catalyst active in catalyzing the synthesis of methanol and the reaction allowed to proceed in the presence of an absorbent capable of absorbing methanol.

7 Claims, 1 Drawing Sheet

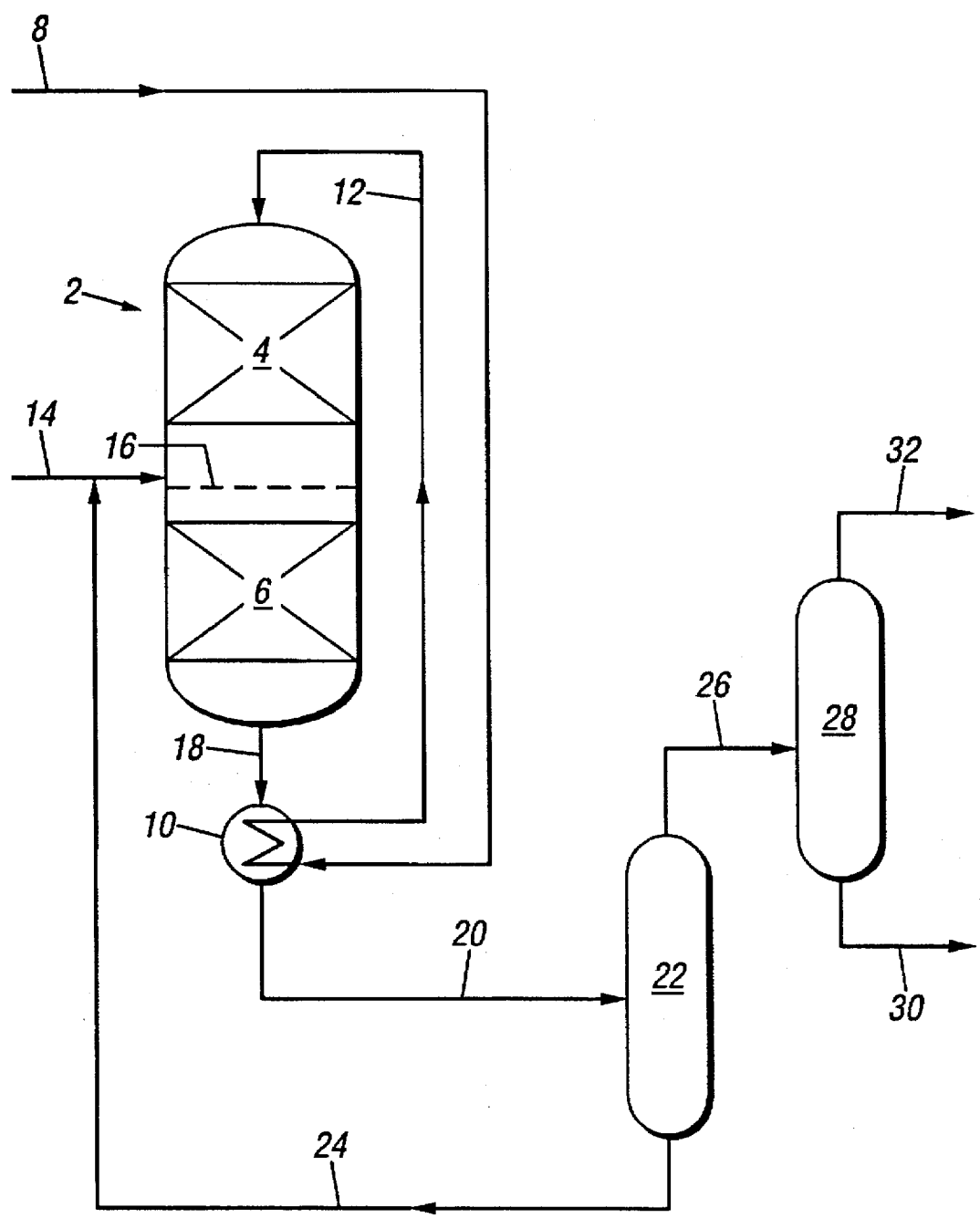

PROCESS FOR CARRYING OUT CHEMICAL EQUILIBRIUM REACTIONS

FIELD OF THE INVENTION

The present invention relates to a process for carrying out chemical equilibrium reactions involving reactants and products which are present as gases under the prevailing reaction conditions. In particular, the present invention is directed to a process for the preparation of methanol, from mixtures of carbon monoxide and hydrogen.

BACKGROUND OF THE INVENTION

A number of chemical process involve chemical reactions which are equilibrium reactions. A number of these reactions involve reactants and products which are gaseous under the prevailing reaction conditions. For such reactions, it has been found possible to select the processing conditions in order to shift the equilibrium of the reaction and favor the formation of the desired end products. One such reaction is the reaction by which methanol is formed from mixtures of carbon monoxide and hydrogen, often referred to as synthesis gas.

Methanol is a valuable material useful, for example as a feed stock for chemical processes. Accordingly, there is a need for a process which may be operated on a commercial scale to produce methanol in high yields with a minimum of by-products. The process should preferably require a minimum of processing equipment and machinery and, therefore, is preferably simple to operate.

One method for preparing methanol is by the reaction of carbon monoxide and hydrogen, mixtures of which are referred to in the art as synthesis gas. The preparation of methanol from carbon monoxide and hydrogen proceeds by means of the following, highly exothermic, equilibrium reaction

$$CO + 2H_2 \rightleftharpoons CH_3OH \qquad (1)$$

In order to achieve an acceptable rate of conversion of carbon monoxide and hydrogen to methanol for operation on a commercial scale, it is necessary to operate the reaction (1) at elevated temperatures. However, the level of conversion achieved is limited by the thermodynamic equilibrium. In order to obtain an acceptably high level of conversion, it has been found necessary to operate the reaction (1) at very high pressures. Operation at the high pressures required is very expensive and requires a large investment in operating plant and machinery.

A number of process schemes have been proposed to accommodate the thermodynamic limitations of chemical equilibrium reactions in general and the methanol synthesis reactions in particular in order to provide attractive processes for commercial application.

The use of an interstage quench to cool the reaction mixture between successive conversion stages and hence favor the forward exothermic reaction yielding methanol has been proposed.

Thus, in U.S. Pat. No. 4,670,473 a synthesis process scheme is disclosed in which synthesis gas is converted in at least two beds of catalyst. Lower alkanols, including methanol, prepared in the process are recycled and used as an interstage quench between successive catalyst beds. U.S. Pat. No. 4,670,473 discloses that, in this way, methanol may be recycled to extinction in order to prepare higher alkanols.

U.S. Pat. No. 4,766,154 discloses a two stage process for the conversion of synthesis gas into methanol. In the process scheme of U.S. Pat. No. 4,766,154, a synthesis gas feed containing carbon dioxide, carbon monoxide and hydrogen, is convened in a first, liquid phase conversion reactor. The product is cooled to condense methanol. The remaining, unconverted synthesis gas is fed to a second liquid phase conversion reactor, the product of which is cooled to yield a methanol product. The operating conditions of the two reactors are selected such that the conversion of carbon monoxide to methanol is favored in the first stage, while the conversion of carbon dioxide to methanol is favored in the second stage.

Several process schemes have been proposed which combine separate liquid phase and gas phase methanol synthesis reactors in the same scheme.

U.S. Pat. No. 4,628,066 discloses a process for the preparation of methanol, in which a synthesis gas feed is passed to a liquid phase methanol synthesis reactor, thereby converting a portion of the feed. The effluent of the reactor is cooled to recover the desired products. Unconverted synthesis gas is passed to a gas phase synthesis reactor for further conversion. Synthesis gas remaining unconverted after this second conversion step is recycled to the inlet of the gas phase reactor.

U.S. Pat. No. 4,946,477 discloses a similar, but more complex, process scheme to that of U.S. 4,628,066. The process scheme of U.S. Pat. No. 4,946,477 comprises a first, liquid phase methanol synthesis stage in which synthesis gas, together with some added water, is converted into methanol. Unconverted synthesis gas is fed to a second conversion stage, in which a gas phase reactor is used to produce additional methanol. Any unconverted synthesis gas remaining is used as fuel and combusted in a gas turbine, thus generating valuable power.

An alternative proposal for overcoming the limitations on conversion and yield imposed upon a commercial operation by thermodynamic equilibrium has been to employ an absorbent for the products of equilibrium reactions, again, in particular, methanol.

European patent application publication No. 326,718 discloses a process for the production of methanol from carbon monoxide and hydrogen, in which the reactants are fed to one or more reaction zones comprising a fixed bed of catalyst using a liquid absorbent to selectively absorb all of the methanol formed. The methanol product is subsequently recovered from the liquid by desorption. EP 326,718 states that the absorption of methanol is preferably effected in a separate absorption zone.

European patent application publication No. 430,699 discloses a further scheme in which an organic absorbent is used to remove methanol from the effluent of a methanol synthesis reactor. EP 430,699 specifically discloses the use of an organic absorbent having between 3 and 16 carbon atoms and which is chemically inert with respect to the product of the synthesis reaction. The mass proportion of absorbent to methanol recovered is less than 10 mass units absorbent for each mass unit of methanol.

Finally, British patent application publication No. 2,255,516 discloses a process for conducting chemical equilibrium reactions, in which a plurality of fluidized bed catalytic reactors are employed in a series flow arrangement. Between at least two consecutive stages, the effluent of one reactor is subjected to an absorption treatment using an inert solvent to remove a product of the reaction. The remaining gaseous stream is fed to the following reactor for further conversion. GB 2,255,516, although not limited in this respect, concentrates on the synthesis of methanol from carbon monoxide and hydrogen.

As will be appreciated, although a number of alternative schemes have been proposed for effecting chemical equilibrium reactions in an optimum manner, there is still a need for a simple, inexpensive process scheme which combines a high degree of conversion and yield of the desired product with a minimum of capital and operating expenditure. Surprisingly, it has been found that a process scheme comprising gas phase reaction stage and a combined reaction and absorption stage offers these advantages.

SUMMARY OF THE INVENTION

Accordingly, the present invention provides a process for carrying out a chemical equilibrium reaction in which, in a first stage, one or more reactants are contacted with a fixed arrangement of a catalyst under conditions such that the reactants and the products of the reaction are gaseous, the unconverted reactants and products of the first stage being passed to a second stage, in which they are contacted with a fixed arrangement of a catalyst and the reaction allowed to proceed in the presence of an absorbent capable of absorbing a product of the reaction.

BRIEF DESCRIPTION OF THE DRAWING

FIG. 1 is a schematic representation of the process for the preparation of methanol from a mixture of carbon monoxide and hydrogen.

DETAILED DESCRIPTION OF THE INVENTION

The process of the present invention is a two stage process. In the first stage, gaseous reactants are contacted with a catalyst. The products of the reaction are gaseous. The catalyst is retained in the form of a fixed arrangement. The catalyst is typically in the form of particles retained in a fixed bed. Suitable techniques for retaining catalysts in fixed bed arrangements are well known in the art. The first stage of the process may comprise one or a plurality of separate reaction stages, in each of which gaseous reactants are contacted with a catalyst to yield gaseous products. The first stage conveniently consists of a single reaction stage.

In the second stage of the process, the products of the first stage, together with the reactants remaining unconverted, are contacted with a catalyst. The catalyst is retained in the form of a fixed arrangement. The catalyst is typically in the form of particles retained in a fixed bed. Suitable techniques for retaining catalysts in fixed bed arrangements are well known in the art. The reaction in the second stage is allowed to proceed in the presence of an absorbent, under conditions such that one or more of the products of the reaction are absorbed. The second stage of the process may comprise one or a plurality of separate reaction stages, in each of which gaseous reactants are contacted with a catalyst to yield gaseous products. The second stage conveniently consists of a single reaction stage.

The products of the reaction, together with any unconverted reactants, are removed from the second stage. The products may be recovered using conventional refining and separation techniques. Unconverted reactants may be recycled to the first stage of the process.

The absorbent, together with the absorbed reaction product, is withdrawn from the second stage. The product may be recovered from the absorbent using conventional desorption techniques well known in the art. The absorbent may be selected so as to absorb one or more than one of the reaction products (in cases in which the reaction yields a plurality of products). In cases in which several reaction products are to be absorbed, the absorbent may comprise one or several different absorbent materials. The absorbent materials may be selected from liquid or solid absorbents. Liquid absorbents may be preferred, as these may be more easily fed to and removed from the second stage in a continuous manner. Solid absorbents may be employed in a continuous trickling mode or, alternatively, in a cycle operation, in which a period of reaction/absorption is followed by a period of desorption and product recovery.

The first and second stages of the process may be carried out in separate reaction vessels. However, a most convenient mode of operation is to employ two fixed catalyst arrangements, one each for the first and second stage, retained within a single reaction vessel.

In general, the yield at the inlet of the first stage of the process, in terms of the mass of product per unit volume of catalyst per hour, will be greater then that at the inlet of the second stage of the process. However, the yield will decrease as the reactants pass through the catalyst in the first stage. This behavior results from effects such as the decrease in the partial pressure of the feed gases through the catalyst bed and from the equilibrium nature of the reactions taking place in the catalyst bed. In contrast, the yield of the second stage of the process remains substantially constant along the entire catalyst bed. However, it is a feature of many reactions when operated under the regime of the second stage of the process of this invention, that the reaction may be limited by mass transfer effects. In such cases, the overall yield of the second stage of the process will be lower than that of the first stage. In such cases, it has been found to be very advantageous if the first and second stages of the process are operated such that the yield of the catalyst at the outlet of the first stage is substantially equal to that at the inlet of the second stage.

The process of the present invention is suitable for carrying our a variety of equilibrium reactions, which are well known in the art. Examples of suitable reactions include the etherification and hydration of olefins to ethers or alcohols, in which the ethers or alcohols are absorbed in the second stage. The process may also be applied in dehydrogenation reactions, such as the dehydrogenation of paraffins to olefins or the dehydrogenation of ethylbenzene to styrene. For these dehydrogenation reactions, an absorbent may be applied in the second stage which will absorb hydrogen or the dehydrogenated product. Alternatively, the process may be applied in carrying out the water gas shift reaction, involving the reaction of water and carbon monoxide to yield hydrogen and carbon dioxide, in which case an absorbent to absorb either carbon dioxide or hydrogen may be used in the second stage.

The process of the present invention has been found to be particularly advantageous when applied in the synthesis of methanol from mixtures of carbon monoxide and hydrogen (commonly known as synthesis gas). Accordingly, in one aspect, the present invention provides a process for the synthesis of methanol from carbon monoxide and hydrogen, in which, in a first stage, carbon monoxide and hydrogen are contacted with a fixed arrangement of a catalyst active in catalyzing the synthesis of methanol under conditions such that the methanol formed is present as a gas under the prevailing reaction conditions, the unconverted carbon monoxide and hydrogen and methanol produced in the first stage being passed to a second stage, in which they are contacted with a fixed arrangement of a catalyst active in catalyzing the synthesis of methanol and the reaction allowed to proceed in the presence of an absorbent capable of absorbing methanol.

Suitable operating conditions for carrying out the aforementioned processes are well known and understood in the art. The general engineering aspects of the two stages of the process of this invention is also readily available in the open literature and well understood in the art. In this respect, reference is made to The Chemical Engineers Handbook, 5th Edition, edited by R. H. Perry and C. H. Chilton.

The process of the present invention will now be described in more detail by reference to the synthesis of methanol from a mixture of carbon monoxide and hydrogen. It is to be appreciated that this description is for illustrative purposes only and that the principles of the process discussed may be applied more generally.

Reference is made to FIG. I, which is a schematic representation of a process for the preparation of methanol from a mixture of carbon monoxide and hydrogen. A reactor, generally indicated as 2, contains a first stage fixed bed of catalyst, 4, and a second stage fixed bed of catalyst 6. Both fixed beds comprise particles of a catalyst active in the synthesis of methanol from carbon monoxide and hydrogen.

A mixture of carbon monoxide and hydrogen is fed via a line 8 to a feed/effluent heat exchanger 10. The mixture of carbon monoxide and hydrogen, heated in the heat exchanger 10 is passed via a line 12 to the inlet of the reactor 2 located above the first stage fixed bed of catalyst 4. The carbon monoxide and hydrogen pass downwards through the catalyst bed 4. The gas leaving the first stage fixed bed of catalyst 4 comprises unconverted carbon monoxide and hydrogen and methanol.

A liquid absorbent is fed via a line 14 to a liquid inlet in the side of the reactor 2 such that the liquid absorbent enters the reactor 2 between the first stage fixed bed of catalyst 4 and the second stage fixed bed of catalyst 6. Once inside the reactor vessel, the liquid absorbent mixes with the gas leaving the first stage fixed bed of catalyst 4. A liquid/gas distributor 16 is located within the reactor 2 below the liquid inlet and above the second stage fixed bed of catalyst 6. The absorbent and the gas are distributed over the top of the second stage fixed bed of catalyst 6 by the distributor 16 and subsequently flow downwards through the bed 6. The effluent leaving the bottom of the reactor comprises a gas phase and a liquid phase. The gas phase comprises unconverted carbon monoxide and hydrogen, together with a very minor amount of methanol vapor. The liquid phase comprises the absorbent and the absorbed methanol.

The effluent leaving the bottom of the reactor 2 passes via a line 18 to the feed/effluent heat exchanger 10. Heat produced by the exothermic reaction of carbon monoxide and hydrogen is recovered by indirect heat exchange in the heat exchanger 10 between the hot effluent leaving the reactor 2 and the fresh feed gas. The thus cooled effluent passes from the heat exchanger 10 via a line 20 to a desorber 22. The desorber 22 acts firstly to separate the gas from the liquid present in the reactor effluent and secondly to separate the methanol product from the absorbent. The absorbent recovered is recycled via a line 24 to the liquid inlet of the reactor 2.

A gaseous stream is recovered from the desorber 22 and is passed via a line 26 to a separator 28. The separator 28 acts to separate unconverted carbon monoxide and hydrogen, together with any minor amounts of by-products which may have been formed, from the methanol product. The methanol product is withdrawn via a line 30. The unconverted carbon monoxide and hydrogen is withdrawn from the separator 28 via a line 32 and may be recycled via a suitable line and compressor (not shown) to the inlet of the reactor 2. A portion of this stream may be removed from the process as a purge, in order to avoid the accumulation of inert components in the recycle loop.

Suitable catalysts for use in the first and second stage fixed beds of catalyst 4 and 6 are well known in the art. Typical methanol synthesis catalysts for use in the process of the present invention are described in the publications described hereinbefore. Examples of suitable methanol synthesis catalysts include catalysts comprising zinc and/or copper as the catalytically active components. The catalyst may comprise a promoter in addition to the catalytically active component, for example aluminum or chromium. The same catalyst may be applied in both the first stage and second stage of the process of this invention.

Suitable operating conditions for the reactor 2 are well known in the art. In order to obtain an acceptable level of catalyst activity, the process is typically operated at elevated temperatures. Suitable temperatures are in the range of from about 100° to about 350° C., more preferably from about 200° to about 300° C. In order to obtain an acceptable level of conversion, the process is preferably operated at elevated pressures. Suitable pressures are in the range of from about 25 to about 200 bar, more preferably from about 50 to about 150 bar.

Suitable absorbents are also well known in the art. Examples of suitable methanol absorbents include alcohols, paraffinic oils, olefinic oils, hydroxylated aromatic solvents and xylenes. In particular, the absorbent may be selected from alcohols having from 3 to 16 carbon atoms, more preferably from 3 to 10 carbon atoms, paraffins and olefins having from 7 to 16 carbon atoms, more preferably from 7 to 10 carbon atoms and hydroxylated aromatic compounds having from 6 to 10 carbons atoms, more preferably 6 to 8 carbon atoms. Especially preferred solvents are tetraethylene glycol dimethyl ether (TEGME), sulfolane and the crown ethers. TEGME is an especially preferred absorbent.

The operating conditions of the desorber 22 will depend upon the specific absorbent selected for use in the process. Typically, the methanol product may be recovered from the absorbent by flashing the liquid stream to a lower pressure, by heating the liquid to a temperature at which the methanol desorbs, or a combination of these, for example by flash distillation. The desorption may be carried out in a single or a multi-stage operation. If the latter is employed, the desorber 22 shown in the Figure can be taken as representing a series of separate desorption stages or vessels. Apparatus for carrying out the desorption stage is well known in the art.

The carbon monoxide and hydrogen used as feed to the methanol synthesis process may be obtained by any of the synthesis gas manufacturing techniques well known in the art. Examples of suitable process include the partial oxidation (combustion), steam reforming and carbon dioxide reforming of a hydrocarbon feed stock. Methane or natural gas is a most suitable and convenient hydrocarbon feed stock. Carbon monoxide and hydrogen are preferably present in the feed at a ratio of hydrogen to carbon monoxide of about 2.

Employing the process scheme as shown in the Figure, a typical hypothetical process scenario is as follows:

The reactor 2 comprises a first and a second fixed bed of catalyst 4 and 6 each comprised of a copper/zinc/alumina catalyst containing 60% wt copper, 25% wt zinc and 15% wt alumina and having an average particle size of 2.0 min. A mixture of carbon monoxide and hydrogen, having a hydrogen to carbon monoxide ratio of 2.0, is introduced via the line 8 into the reactor 2 at a pressure of 80 bar and a gas hourly space velocity of 3000 Nl gas/l catalyst/hour. The reactor 2 is operated at a temperature of 280° C. The first stage fixed bed of catalyst has a space time yield of methanol (STY) of 4.6 kg/m$^3$/s at its inlet and an STY of 1.5 kg/m$^3$/s at its outlet.

The effluent from the first stage fixed bed of catalyst is mixed with TEGME supplied to the liquid inlet of the reactor 2 at a flowrate sufficient to absorb substantially all the methanol produced in the second stage and fed via the distributor 16 to the upper portion of the second stage fixed bed of catalyst 6. The second stage fixed bed of catalyst 6 has a constant STY of 1.5 kg/m$^3$/s throughout its length. The two catalyst beds combined exhibit an overall STY of 2 kg/m$^3$/s.

What is claimed is:

1. A process for carrying out a chemical equilibrium reaction in which, in a first stage, one or more reactants are contacted with a fixed arrangement of a catalyst under conditions such that the reactants and the products of the reaction are gaseous, the unconverted reactants and products of the first stage being passed to a second stage, in which they are contacted with a fixed arrangement of a catalyst and the reaction allowed to proceed in the presence of an absorbent capable of absorbing a product of the reaction; and wherein the two fixed beds of catalyst arrangements are retained within a single reaction vessel.

2. The process according to claim 1 wherein that the first stage consists of a single reaction stage.

3. The process according to claim 2 wherein the second stage consists of a single reaction stage.

4. The process according to claim 3 wherein the first and second stages are operated such that the yield, in terms of the mass of product per unit volume of catalyst per hour, at the outlet of the first stage is substantially equal to the yield at the inlet of the second stage.

5. The process according to claim 4 wherein the reaction is selected from the etherification or hydration of olefins, a dehydrogenation reaction, the water gas shift reaction and the synthesis of methanol.

6. The process according to claim 5 for the synthesis of methanol from carbon monoxide and hydrogen, in which, in a first stage, carbon monoxide and hydrogen are contacted with a fixed arrangement of a catalyst active in catalyzing the synthesis of methanol under conditions such that the methanol formed is present as a gas under the prevailing reaction conditions, the unconverted carbon monoxide and hydrogen and methanol produced in the first stage being passed to a second stage, in which they are contacted with a fixed arrangement of a catalyst active in catalyzing the synthesis of methanol and the reaction allowed to proceed in the presence of an absorbent capable of absorbing methanol.

7. The process according to claim 6 wherein the absorbent used in the second stage is a liquid selected from the group consisting of tetraethylene glycol dimethyl ether, sulfolane and a crown ether.

* * * * *